United States Patent
Kubo et al.

(10) Patent No.: US 6,597,456 B2
(45) Date of Patent: Jul. 22, 2003

(54) MEASURING CHIP FOR QUANTITATIVE ANALYSIS OF SUBSTANCES

(75) Inventors: Takashi Kubo, Kaisei-machi (JP); Masayuki Naya, Kaisei-machi (JP)

(73) Assignee: Fuji Photo Film Co., Ltd., Kanagawa-Ken (JP)

(*) Notice: Subject to any disclaimer, the term of this patent is extended or adjusted under 35 U.S.C. 154(b) by 59 days.

(21) Appl. No.: 09/851,957

(22) Filed: May 10, 2001

(65) Prior Publication Data

US 2001/0040680 A1 Nov. 15, 2001

(30) Foreign Application Priority Data

| May 11, 2000 | (JP) | ............................. 2000-138604 |
| Jul. 13, 2000 | (JP) | ............................. 2000-212125 |
| Jan. 25, 2001 | (JP) | ............................. 2001-016633 |
| Mar. 28, 2001 | (JP) | ............................. 2001-092666 |

(51) Int. Cl.[7] .............................................. G01N 21/55
(52) U.S. Cl. ..................... 356/445; 356/246; 250/239; 250/573
(58) Field of Search ................................ 356/445, 246, 356/244, 318; 422/58, 55, 50, 68.1, 82.05; 435/808, 4; 436/43, 47, 165, 805; 250/239, 573, 574, 576

(56) References Cited

U.S. PATENT DOCUMENTS 5,055,265 A * 10/1991 Finlan ........................ 356/318
5,374,563 A * 12/1994 Maule ........................ 356/318
6,104,484 A * 8/2000 Nagata et al. .............. 356/246

FOREIGN PATENT DOCUMENTS

| EP | 0 884 581 A1 | 12/1998 | .......... G01N/21/55 |
| JP | 6-167443 | 6/1994 | .......... G01N/21/27 |
| JP | 9-257701 | 10/1997 | .......... G01N/21/27 |
| WO | WO 95/22754 | 8/1995 | |
| WO | 97/15819 | 5/1997 | .......... G01N/21/55 |
| WO | 99/44042 | 9/1999 | .......... G01N/21/55 |

OTHER PUBLICATIONS

Takayuki Okamoto; "Spectrum Researches"; vol. 47, No. 1; 1997, pp. 19 Dec.

* cited by examiner

Primary Examiner—Kevin Pyo
Assistant Examiner—Seung C. Sohn
(74) Attorney, Agent, or Firm—Sughrue Mion, PLLC (57) ABSTRACT

A measuring apparatus includes a dielectric block, a film layer which is formed on a first face of the dielectric block and is brought into contact with a sample, an optical system which causes a light beam to enter the dielectric block through a second face so that the light beam is reflected in total internal reflection at the interface of the dielectric block and the film layer and various angles of incidence of the light beam to the interface can be obtained, and a photodetector which detects the intensity of the light beam which is reflected in total internal reflection at the interface and goes outside the dielectric block through a third face thereof. A measuring chip includes a single dielectric block having all the first to third faces and the film layer integrally formed on the first face of the dielectric block.

18 Claims, 10 Drawing Sheets

MEASURING CHIP FOR QUANTITATIVE ANALYSIS OF SUBSTANCES

BACKGROUND OF THE INVENTION

1. Field of the Invention

This invention relates to a measuring chip for use in, for instance, a surface plasmon resonance sensor for quantitatively analyzing a material in a sample utilizing generation of surface plasmon.

2. Description of the Related Art

In metal, free electrons vibrate in a group to generate compression waves called plasma waves. The compression waves generated in a metal surface are quantized into surface plasmon.

There have been proposed various surface plasmon resonance sensors for quantitatively analyzing a material in a sample utilizing a phenomenon that such surface plasmon is excited by light waves. Among those, one employing a system called "Kretschmann configuration" is best known. See, for instance, Japanese Unexamined Patent Publication No. 6(1994)-167443.

The plasmon resonance sensor using the Kretschmann configuration basically comprises a dielectric block shaped, for instance, like a prism, a metal film which is formed on one face of the dielectric block and is brought into contact with a sample, a light source emitting a light beam, an optical system which causes the light beam to enter the dielectric block so that the light beam is reflected in total internal reflection at the interface of the dielectric block and the metal film and various angles of incidence of the light beam to the interface of the dielectric block and the metal film including an angle of incidence at which surface plasmon is generated can be obtained, and a photodetector means which is able to detect the intensity of the light beam reflected in total internal reflection at the interface and detect a state of surface plasmon resonance.

In order to obtain various angles of incidence of the light beam to the interface, a relatively thin incident light beam may be caused to impinge upon the interface while deflecting the incident light beam or a relatively thick incident light beam may be caused to impinge on the interface in the form of convergent light or divergent light so that components of the incident light beam impinge upon the interface at various angles. In the former case, the light beam which is reflected from the interface at an angle which varies as the incident light beam is deflected may be detected by a photodetector which is moved in synchronization with deflection of the incident light beam or by an area sensor extending in the direction in which reflected light beam is moved as a result of deflection. In the latter case, an area sensor which extends in directions so that all the components of light reflected from the interface at various angles can be detected by the area sensor may be used.

In such a plasmon resonance sensor, when a light beam impinges upon the interface at a particular angle of incidence θsp not smaller than the angle of total internal reflection, evanescent waves having an electric field distribution in the sample in contact with the metal film are generated and surface plasmon is excited in the interface between the metal film and the sample. When the wave vector of the evanescent waves is equal to the wave number of the surface plasmon and wave number matching is established, the evanescent waves and the surface plasmon resonate and light energy is transferred to the surface plasmon, whereby the intensity of light reflected in total internal reflection at the interface of the dielectric block and the metal film sharply drops. The sharp intensity drop is generally detected as a dark line by the photodetector.

The aforesaid resonance occurs only when the incident light beam is p-polarized. Accordingly, it is necessary to set the light beam to impinge upon the interface in the form of p-polarized light.

When the wave number of the surface plasmon can be known from the angle of incidence θsp at which the phenomenon of attenuation in total internal reflection (ATR) takes place, the dielectric constant of the sample can be obtained. That is, $$K_{sp}(\omega) = \frac{\omega}{c} \sqrt{\frac{\varepsilon_m(\omega)\varepsilon_s}{\varepsilon_m(\omega) + \varepsilon_s}}$$

wherein $K_{sp}$ represents the wave number of the surface plasmon, ω represents the angular frequency of the surface plasmon, c represents the speed of light in a vacuum, and ∈ m and ∈ s respectively represent the dielectric constants of the metal and the sample.

When the dielectric constant ∈ s of the sample is known, the concentration of a specific material in the sample can be determined on the basis of a predetermined calibration curve or the like. Accordingly, a specific component in the sample can be quantitatively analyzed by detecting the angle of incidence θsp at which the intensity of light reflected in total internal reflection from the interface of the prism and the metal film sharply drops.

In the conventional plasmon resonance sensor of the type described above employing the system described above, it is practically necessary to change sample by sample the metal film to be brought into contact with the sample. Conventionally, the metal film is fixedly formed on a flat and thin dielectric plate as a unit and the unit is removably integrated with a prism-like dielectric block which functions as an optical coupler for causing total internal reflection. The prism-like dielectric block is fixedly provided with respect to the optical system and the unit of the metal film and the dielectric plate is changed sample by sample as a measuring chip.

As a similar apparatus utilizing the phenomenon of attenuation in total internal reflection (ATR), there has been known a leaky mode sensor described in, for instance, "Spectrum Researches" Vol.47, No.1 (1998), pp21 to 23 & pp26 and 27. The leaky mode sensor basically comprises a dielectric block shaped, for instance, like a prism, a clad layer which is formed on one face of the dielectric block, an optical waveguide layer which is formed on the clad layer and is brought into contact with a sample, a light source emitting a light beam, an optical system which causes the light beam to enter the dielectric block at various angles of incidence so that total internal reflection conditions are satisfied at the interface of the dielectric block and the clad layer, and a photodetector means which is able to detect the intensity of the light beam reflected in total internal reflection at the interface and detect an excited state of waveguide mode, i.e., attenuation in total internal reflection (ATR).

In the leaky mode sensor with this arrangement, when the light beam is caused to impinge upon the clad layer through the dielectric block at an angle not smaller than an angle of total internal reflection, only light having a particular wave number and impinging upon the optical waveguide layer at a particular angle of incidence comes to propagate through the optical waveguide layer in a waveguide mode after passing through the clad layer. When the waveguide mode is thus excited, almost all the incident light is taken in the optical waveguide layer and accordingly, the intensity of light reflected in total internal reflection at the interface of the dielectric block and the clad layer sharply drops. That is, attenuation in total internal reflection occurs. Since the wave number of light to be propagated through the optical waveguide layer in a waveguide mode depends upon the refractive index of the sample on the optical waveguide layer, the refractive index and/or the properties of the sample related to the refractive index can be detected on the basis of the angle of incidence at which the attenuation in total internal reflection occurs.

Also in the leaky mode sensor, it is possible to fix a dielectric block with respect to the optical system, to form the clad layer and the optical waveguide layer on another dielectric block to form a measuring chip, and to change the measuring chip sample by sample.

However, when the conventional measuring chips are used, the dielectric blocks have to be integrated with each other by way of refractive index matching fluid in order to prevent a space from being formed between the dielectric blocks to make discontinuous the refractive index between the blocks. Such operation is very troublesome, which makes the conventional measuring chips inconvenient to handle. Especially, in an automated measuring system in which a plurality of measuring chips are loaded on a turret and the turret is rotated to bring the measuring chips in sequence to a measuring position where a light beam is projected onto each measuring chip, loading and unloading the measuring chips take a lot of labor, which is apt to cause deterioration in the measuring efficiency.

Further, the refractive index matching fluid can adversely affect the environment.

SUMMARY OF THE INVENTION

In view of the foregoing observations and description, the primary object of the present invention is to provide a measuring chip which is easily replaceable and can eliminate necessity of using refractive index matching fluid.

In accordance with a first aspect of the present invention, there is provided a measuring chip which is used in a measuring apparatus comprising a dielectric block, a film layer which is formed on a first face of the dielectric block and is brought into contact with a sample, a light source which emits a light beam, an optical system which causes the light beam to enter the dielectric block through a second face thereof so that the light beam is reflected in total internal reflection at the interface of the dielectric block and the film layer and various angles of incidence of the light beam to the interface of the dielectric block and the film layer can be obtained, and a photodetector means which detects attenuation in total internal reflection by detecting the intensity of the light beam which is reflected in total internal reflection at the interface and goes outside the dielectric block through a third face thereof, the measuring chip comprising a single dielectric block having all the first to third faces and the film layer integrally formed on the first face of the dielectric block.

In accordance with a second aspect of the present invention, there is provided a measuring chip which is used especially in a surface plasmon resonance sensor comprising a dielectric block, a metal film layer which is formed on a first face of the dielectric block and is brought into contact with a sample, a light source which emits a light beam, an optical system which causes the light beam to enter the dielectric block through a second face thereof so that the light beam is reflected in total internal reflection at the interface of the dielectric block and the metal film and various angles of incidence of the light beam to the interface of the dielectric block and the metal film can be obtained, and a photodetector means which detects attenuation in total internal reflection due to plasmon resonance by detecting the intensity of the light beam which is reflected in total internal reflection and goes outside the dielectric block through a third face thereof, the measuring chip comprising a single dielectric block having all the first to third faces and the metal film layer integrally formed on the first face of the dielectric block.

In accordance with a third aspect of the present invention, there is provided a measuring chip which is used especially in a leaky mode sensor comprising a dielectric block, a film layer composed of a clad layer which is formed on a first face of the dielectric block and an optical waveguide layer which is formed on the clad layer and is brought into contact with a sample, a light source which emits a light beam, an optical system which causes the light beam to enter the dielectric block through a second face thereof so that the light beam is reflected in total internal reflection at the interface of the dielectric block and the metal film and various angles of incidence of the light beam to the interface of the dielectric block and the metal film can be obtained, and a photodetector means which detects attenuation in total internal reflection due to excitation of waveguide mode in the optical waveguide layer by detecting the intensity of the light beam which is reflected in total internal reflection and goes outside the dielectric block through a third face thereof, the measuring chip comprising a single dielectric block having all the first to third faces and the metal film layer integrally formed on the first face of the dielectric block.

These measuring chips are preferably provided with a sample holder mechanism for holding the sample on the film layer. Specifically, the sample holder mechanism may comprise a member which defines above the film layer a space having closed side walls. It is further preferred that the space is flared upward. In this case, it is preferred that the inner surface of the member which defines above the film layer a space having closed side walls is smoothly merged with the first face of the dielectric block on which the film layer is formed.

Further it is preferred that the dielectric block be polygonal such as a rectangle in a horizontal cross-section. In this specification, "the horizontal cross-section" means a cross-section taken along a plane perpendicular to the vertical direction of the block in which the block is positioned in operation of the measuring chip.

When the dielectric block is polygonal in a horizontal cross-section, it is preferred that corners of the polygonal be rounded in at least one horizontal plane. The polygonal may be rounded at corners between two adjacent side surfaces thereof, at corners between two adjacent side surfaces and the bottom surface, and at both the corners.

Further, when the dielectric block is polygonal in a horizontal cross-section, it is preferred that the dielectric block is tapered downward so that the cross-sectional area becomes larger upward. In this case, it is preferred that the inclined side surfaces of the dielectric block be at 3 to 15° to the vertical axis of the dielectric block.

Preferably the dielectric block is formed of, for instance, glass or transparent resin. When the dielectric block is formed of transparent resin, it is preferred that the sample holder mechanism be formed integrally with the dielectric block.

Further, it is preferred that a sensing medium which makes bonding reaction with a particular material in the sample be fixed on the film layer.

In the measuring chip in accordance with the present invention since the single dielectric block has all the light incident face, the light emanating face and the face on which the film layer is formed and functions as an optical coupler, the measuring chip need be coupled with or decoupled from another member and accordingly, can be easily and quickly replaced.

That is, unlike the prior art, the measuring chip of the present invention need not be coupled with another dielectric block (as an optical coupler) by way of refractive index matching fluid, and accordingly it is very easy to handle.

Further, since it is not necessary to use the refractive index matching fluid, adverse influence of the fluid on the environment can be avoided.

When the sample holder mechanism comprises a member which defines above the film layer a space which has closed side walls and is flared upward, the film layer can be uniform in thickness. That is, since the film layer is generally formed by deposition, when the sample holder mechanism is of such a shape, the film layer can be uniformly formed without being adversely affected by the sample holder mechanism.

Further, when the inner surface of the member which defines above the film layer a space having closed side walls is smoothly merged with the first face of the dielectric block on which the film layer is formed, plastic injection molding of the dielectric block/sample holder mechanism unit is facilitated since ejection of the products from the injection mold becomes smoother, whereby defective products can be reduced.

When the dielectric block is polygonal in a horizontal cross-section and the corners of the polygonal are rounded in at least one horizontal plane, plastic injection molding of the dielectric block/sample holder mechanism unit is facilitated since ejection of the products from the injection mold becomes smoother, whereby defective products can be reduced.

Further, when the dielectric block is polygonal in a horizontal cross-section and is tapered downward so that the cross-sectional area becomes larger upward, positioning of the measuring chip on the measuring apparatus is facilitated.

That is, by forming a plurality of polygonal holes in a horizontal table of the measuring apparatus and holding the measuring chips by inserting the chips into the holes, the dielectric block can be automatically set in a predetermined direction in a horizontal plane and held there through engagement of polygons.

By the same arrangement, the measuring chips can be automatically positioned also in the vertical direction.

These inventors have found that when the inclined side surfaces of the dielectric block is at 3 to 15° to the vertical axis of the dielectric block, the measuring chip can be especially accurately positioned, the reason for which will become apparent later.

DESCRIPTION OF THE PREFERRED EMBODIMENTS

Figure 1:
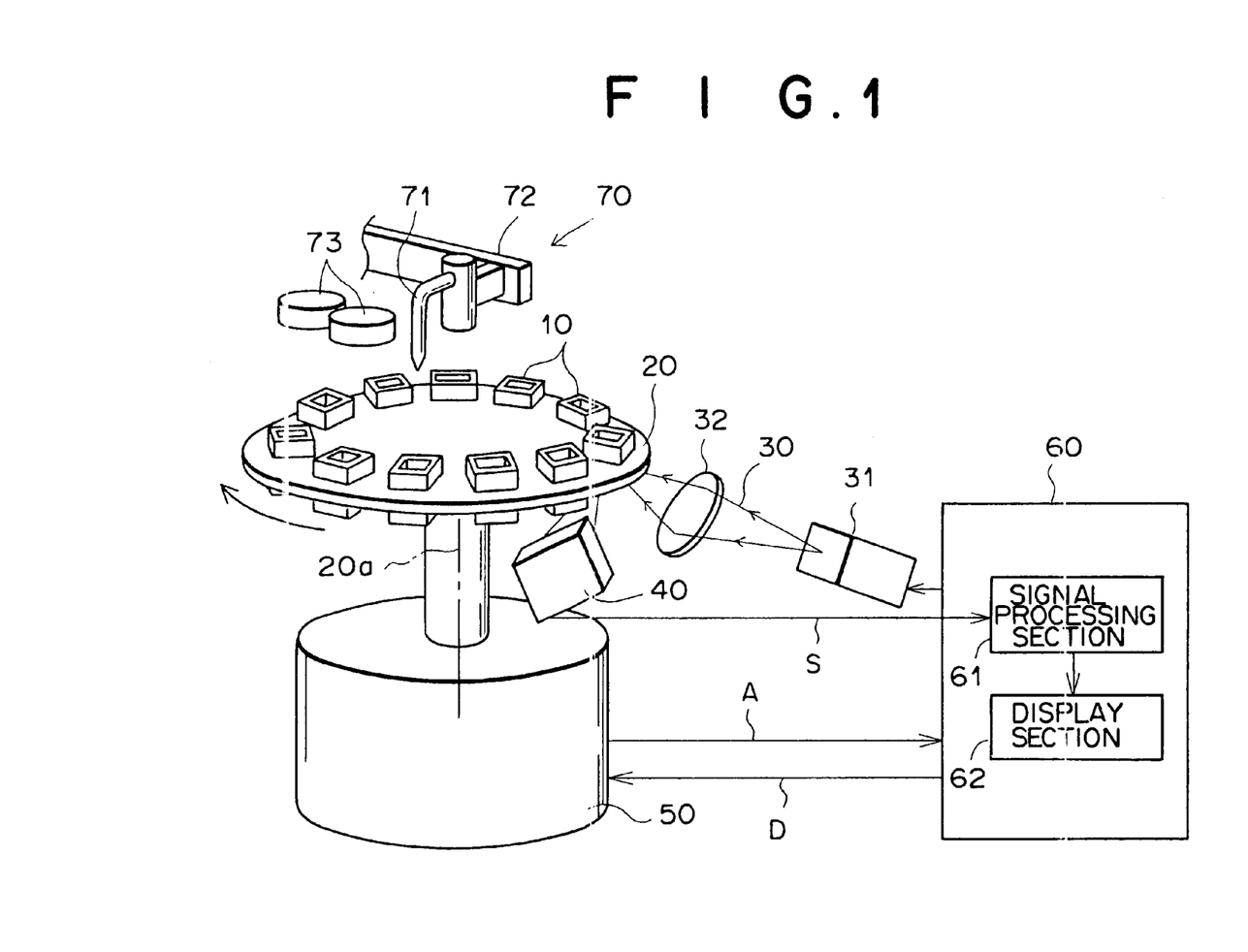
FIG. 1 is a plan view of a surface plasmon resonance sensor employing a measuring chip in accordance with a first embodiment of the present invention.
Figure 2:
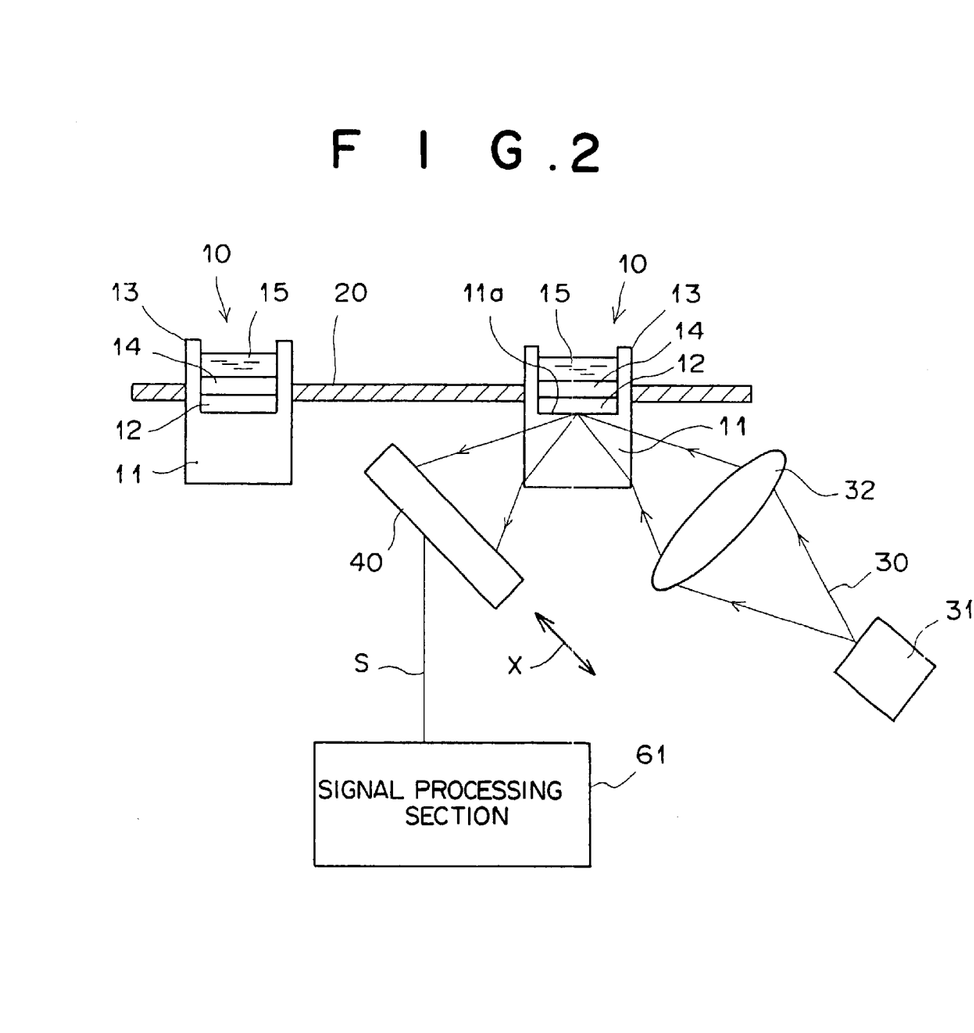
FIG. 2 is a fragmentary side view showing a part of the surface plasmon resonance sensor.
Figure 3:
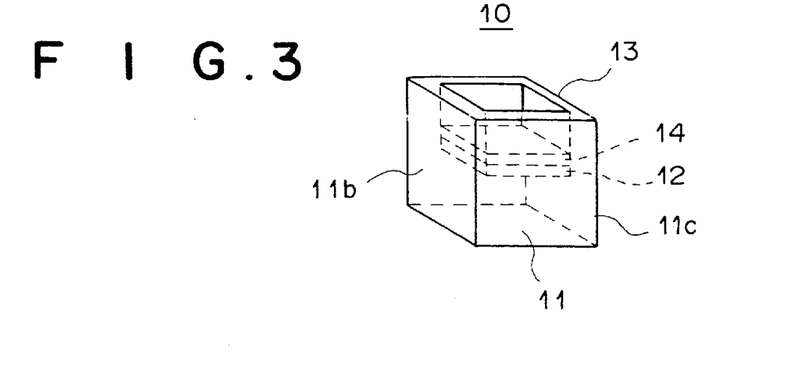
FIG. 3 is a perspective view showing the measuring chip of the first embodiment.

In FIGS. 1 to 3, a surface plasmon resonance sensor comprises a turn table 20 on which a plurality of measuring chips 10 in accordance with a first embodiment of the present invention are supported, a laser 31 such as a semiconductor laser which emits a measuring light beam 30, a condenser lens 32 which forms an incident optical system, a photodetector 40, a drive means 50 which intermittently rotates the turn table 20, a controller 60 which controls the drive means 50 and at the same time receives output signal S of the photodetector 40 to execute processing described later, and an automatic sample supply mechanism 70.

As shown in FIGS. 2 and 3, each of the measuring chips 10 comprises a transparent dielectric block 11 which is rectangular in shape, a metal film 12 such as of gold, silver, cupper, aluminum or the like which is formed on the upper face of the block 11, and a sample holder frame 13 which is a tubular member defining above the metal film 12 a space having closed side walls. The dielectric block 11 is of a single piece which has all the face on which the metal film 12 is formed (a face forming an interface 11a to be described later), a light incident face 11 through the measuring light beam 30 enters the block 11 and a light emanating face 11c through which the measuring light beam 30 emanates the block 11. In the sample holder frame 13 is stored, for instance, a sample liquid 15 in the manner to be described later.

The measuring chip 10 is formed, for instance, by integrally forming the dielectric block 11 and the sample holder frame 13 by injection molding of transparent resin and is replaceable. In this particular embodiment, the measuring chips 10 are removably held in through holes formed in the turn table 20. Further, in this particular embodiment, a sensing medium 14 is fixed on the metal film 12. The sensing medium 14 will be described later.

As the transparent resin for forming the dielectric block 11 and the sample holder frame 13, PMMA, polycarbonate, amorphous polyolefin, cycloolefin and the like are preferred. Also glass may be preferably employed. As the material for forming the dielectric block 11, those which are 1.45 to 2.5 or so in refractive index are generally preferred since a practical SPR angle is obtained in the refractive index range.

The turn table 20 is arranged so that a plurality of (eleven in this particular embodiment) measuring chips 10 are supported on a circle about its axis of rotation 20a at regular intervals. The drive means 50 comprises a stepping motor and rotates the turn table 20 by an angle equal to the angular space between the chips 10.

As shown in FIG. 2, the condenser lens 32 condenses the light beam 30 and caused to enter the dielectric block 11 in the form of a convergent light beam so that various angles of incidence of the light beam 30 to the interface 11a of the dielectric block 11 and the metal film 12 can be obtained. The range of the angles of incidence is set to include a range in which the total internal reflection condition of the light beam 30 is satisfied at the interface 11a and a surface plasmon resonance can take place.

The light beam 30 impinges upon the interface 11a in the form of p-polarized light. This can be realized by suitably positioning the laser 31 or by control the polarization direction of the light beam 30 by the use of a wavelength plate, a polarizing plate or the like.

The photodetector 40 comprises a line sensor having a number of photodetector elements arranged in a row in the direction arrow X in FIG. 2.

The controller 60 receives an address signal A representing the position of the drive means 50 and outputs a drive signal D for driving the drive means 50 on the basis of a predetermined sequence. Further, the controller 60 is provided with a signal processing section 61 which receives an output signal S from the photodetector 40 and a display section 62 which receives an output of the signal processing section 61.

The automatic sample supply mechanism 70 includes a pipette 71, which sucks a predetermined amount of sample liquid and a pipette drive means 72, which moves the pipette 71. The automatic sample supply mechanism 70 causes the pipette 72 to suck the sample in a sample container 73 held in a predetermined position and moves the pipette 71 above the sample holder frame 13 of a measuring chip 10 in a predetermined position, and causes the pipette 71 to spot the sample liquid in the sample holder frame 13.

Operation of the surface plasmon resonance sensor will be described hereinbelow. The turn table 20 is intermittently rotated by the drive means 50. When the turn table 20 is stopped, sample liquid 15 is supplied to the sample holder frame 13 of the measuring chip 10 in the predetermined position by the automatic sample supply mechanism 15.

When a measuring chip 10 the sample holder frame 13 of which contains therein the sample liquid 15 is stopped in a predetermined measuring position (the position of the right side measuring chip 10 in FIG. 2), the laser 31 is driven under the control of the controller 60 and the light beam 30 emitted from the laser 31 impinges upon the interface 11a between the dielectric block 11 and the metal film 12 in the form of convergent light. The light beam 30 is reflected in total internal reflection at the interface 11a and is detected by the photodetector 40.

Since the light beam 30 impinges upon the interface 11a in the form of convergent light, the light beam 30 includes components which impinge upon the interface at various angles $\theta$. The angles $\theta$ of incidence is not smaller than the angle of total internal reflection. Accordingly, the light beam 30 is reflected in total internal reflection at the interface 11a, and the reflected light beam 30 at the interface 11a includes components reflected at various reflecting angles. The optical system such as the condenser lens 32 may be arranged so that the light beam 30 impinges upon the interface 11 in a defocused state. This arrangement is advantageous in that errors in detecting the state of surface plasmon resonance, e.g., in detecting the position of the aforesaid dark line, are averaged, whereby the measuring accuracy is enhanced.

Figure 4:
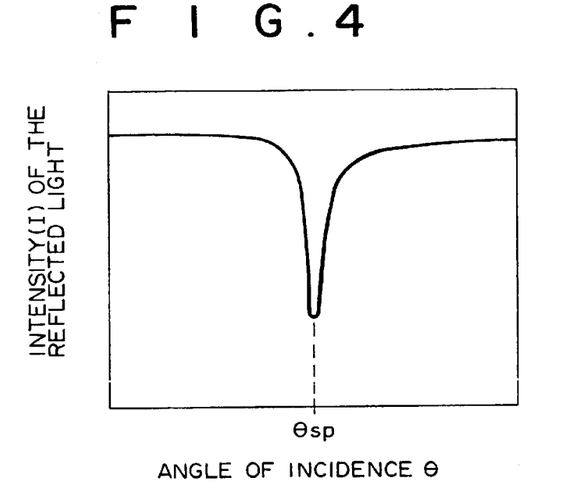
FIG. 4 is a graph showing the relation between the angle of incidence of a light beam and the output of the photodetector.

When the light beam 30 is reflected in total internal reflection at the interface 11a, evanescent waves ooze out from the interface 11a toward the metal film 12 and excite surface plasmon on the surface of the metal film 12. The component of the light beam 30 which impinges upon the interface at a specified angle $\theta$sp resonate with the surface plasmon excited on the surface of the metal film 12 and accordingly, the intensity I of the component of the light beam 30 reflected in total internal reflection at the interface 11a sharply drops. FIG. 4 is a graph showing the relation between the angle of incidence $\theta$sp of the light beam 30 and the output (I) of the photodetector 40.

By detecting the amount of reflected light received by each photodetector element on the basis of the output signal of the photodetector 40, the position of the photodetector element which detects the dark line can be determined and the angle θsp of incidence at which the intensity I of the light beam 30 reflected in total internal reflection at the interface 11a sharply drops can be determined. Accordingly by referring to a standard curve which represents the relation between the intensity I of the reflected light and the angle θsp of incidence at which the intensity I of the light beam 30 reflected in total internal reflection at the interface 11a sharply drops for each sample, a particular material in the sample 15 can be quantitatively analyzed. The signal processing section 61 of the controller 60 quantitatively analyzes the particular material in the sample 15 on the basis of this fact and the result of the analysis is displayed by the display section 62.

When each sample 15 is subjected to measurement only once, the measuring chips 10 may be manually or automatically removed from the turn table 20. Whereas when each sample 15 is subjected to measurement a plurality of times, the measuring chips 10 may be left on the turn table 20 so that the measuring chip 20 is brought to the measuring position again when the turn table 20 makes another rotation.

As described above, in the surface plasmon resonance sensor of this embodiment, since a plurality of measuring chips 10 are held on the turn table 20 and the turn table 20 is intermittently rotated so that the measuring chips 10 are brought to the measuring position in sequence, a plurality of samples 15 can be measured at a high efficiency whereby the time required to measure each sample can be shortened.

Further, since, in this particular embodiment, the automatic sample supply mechanism 70 is provided, the time required to supply samples to the measuring chips 10 also can be shortened, whereby the time required to measure each sample can be further shortened.

Further, by replacing by a new measuring chip 10 a measuring chip 10 holding the sample 15 which is already measured, new samples 15 can be measured immediately, whereby the time required to measure a plurality of samples can be further shortened.

Further since, unlike the prior art, the measuring chip 10 of this embodiment need not be coupled with another dielectric block (as an optical coupler) by way of refractive index matching fluid, it is very easy to handle. Further, since it is not necessary to use the refractive index matching fluid, adverse influence of the fluid on the environment can be avoided.

The sensing medium 14 fixed on the surface of the metal film 12 is selectively linked to a specific material in the sample 15. As such a combination of the sensing medium 14 and the specific material in the sample 15, for instance, combinations of antigen and antibody are known. In such a case, antigen-antibody reaction can be detected on the basis of the angle θsp of total internal reflection attenuation.

Figure 5:
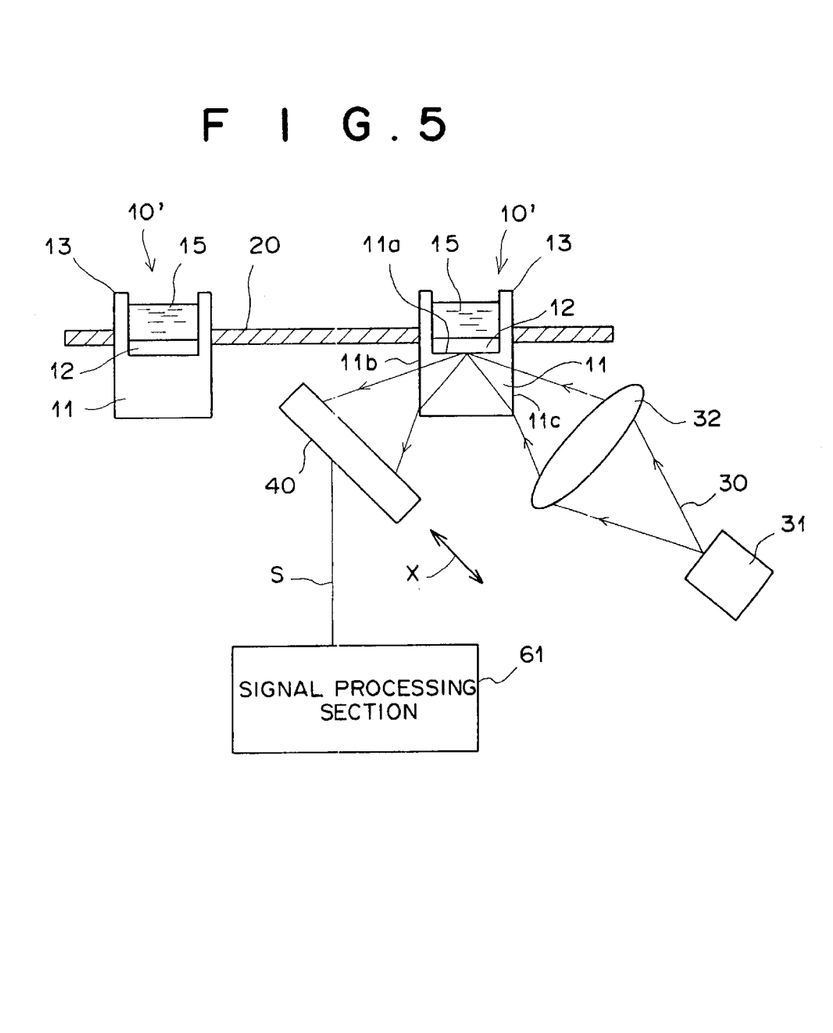
FIG. 5 is a side view partly cut away of a surface plasmon resonance sensor employing a measuring chip in accordance with a second embodiment of the present invention.

FIG. 5 shows a measuring chip 10' in accordance with a second embodiment of the present invention and a surface plasmon resonance sensor employing the measuring chip 10' of the second embodiment. In FIG. 5, elements analogous to those shown in FIG. 2 are given the same reference numerals and will not be described here.

The measuring chip 10' of the second embodiment differs from the measuring chip 10 of the first embodiment in that the measuring chip 10' is not provided with the sensing medium 14. Accordingly, in the second embodiment, the specific material in the sample 15 is not linked with the sensing medium and the normal quantitative analysis of a material to be measured in the sample 15 is effected.

Except this point, the measuring chip 10' of the second embodiment is the same as the measuring chip 10 of the first embodiment shown in FIGS. 2 and 3.

Figure 6:
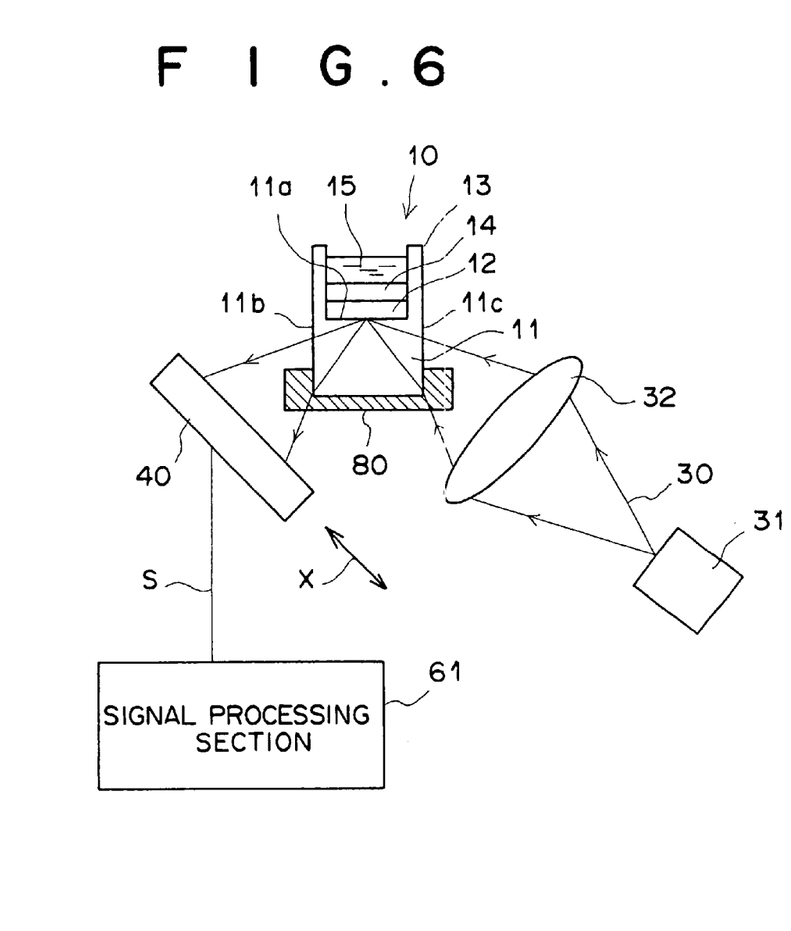
FIG. 6 is a side view partly cut away of another example of a surface plasmon resonance sensor which can employ a measuring chip in accordance with the present invention.

Though, in the first and second embodiments described above, the measuring chip of the present invention is employed in an apparatus where a plurality of the measuring chips are mounted on the turn table 20 and automatically brought to and removed from the measuring position by rotating the turn table 20, the measuring chip of the present invention can be employed in a measuring apparatus where such an automatic measuring chip supply mechanism is not provided. For example, the surface plasmon resonance sensor shown in FIG. 6 comprises an attachment 80 which is fixed with respect to the laser 31, the condenser lens 31 and the photodetector 40. In the surface plasmon resonance sensor shown in FIG. 6, the measuring chip 10 is manually set to the attachment 80, and after measurement, the measuring chip 10 is manually replaced by new one.

Third to eleventh embodiments of the present invention will be described with reference to FIGS. 7 to 17B, hereinbelow.

Figure 7:
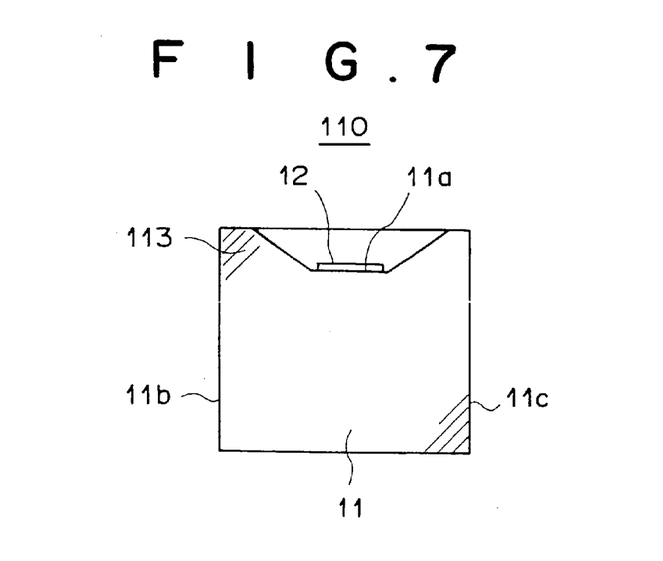
FIG. 7 is a side cross-sectional view of a measuring chip in accordance with a third embodiment of the present invention.

The measuring chip 110 of the third embodiment of the present invention shown in FIG. 7 is the same as the measuring chip 10 of the first embodiment in shape of the dielectric block 11 but different from that in shape of the sample holder frame. That is, in the measuring chip 110, the space inside the sample holder frame 113 is flared upward. Since the metal film 12 is generally formed by deposition, when the sample holder mechanism 113 is of such a shape, the metal film 12 can be formed in a uniform thickness without being adversely affected by the sample holder frame 113.

Figure 8:
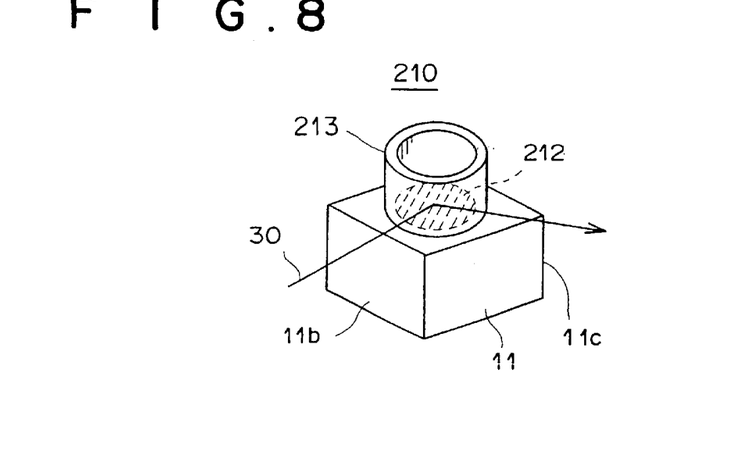
FIG. 8 is a perspective view of a measuring chip in accordance with a fourth embodiment of the present invention.

The measuring chip 210 of the fourth embodiment shown in FIG. 8 differs from that of the first embodiment shown in FIG. 3 in that the sample holder frame 213 is cylindrical and the metal film 212 is circular.

Figure 9:
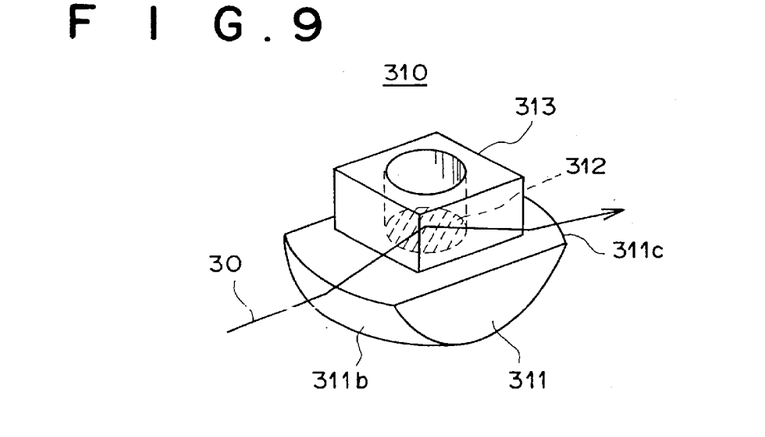
FIG. 9 is a perspective view of a measuring chip in accordance with a fifth embodiment of the present invention.

In the measuring chip of the fifth embodiment shown in FIG. 9, the sample holder frame 313 has a cylindrical inner space though is rectangular in outer shape. The metal film 312 is circular. Further the dielectric block 311 has a spherical light incident face 311b and a spherical light emanating face 311c. The light incident face 311b and the light emanating face 311c of the dielectric block 311 function like a lens to the light beam 30.

Figure 10:
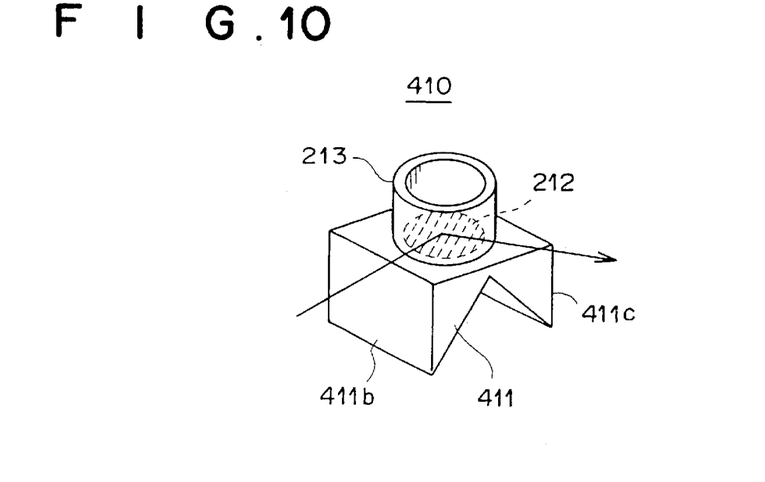
FIG. 10 is a perspective view of a measuring chip in accordance with a sixth embodiment of the present invention.

The measuring chip 410 of the sixth embodiment shown in FIG. 10 differs from that 210 of the fourth embodiment shown in FIG. 8 in the shape of the dielectric block 411. That is, in this embodiment, a part of the dielectric block 411 outside the optical path of the light beam 30 is cut away. With this arrangement, the material for forming the dielectric block can be saved.

The measuring chip 510 of the seventh embodiment and a surface plasmon resonance sensor in which the measuring chip 510 of the seventh embodiment is employed will be described with reference to FIG. 11, hereinbelow. The measuring chip 510 comprises a dielectric block 511 formed of transparent resin. The dielectric block 511 is of a quadrangular pyramid in outer shape which flares upward and is positioned with the smaller side down when it is set on the surface plasmon resonance sensor.

Out of the four side faces of the dielectric block 511, two side faces form a light incident face 511b and a light emanating face 511c. The light incident face 511b and the light emanating face 511c of the dielectric body 511 may be transparent over the entire area or may be transparent only the part through which the light beam 30 travels. The other two faces may be transparent over the entire area or may be transparent only the part through which the light beam 30 travels, or may be semitransparent.

A sample holder hole 511m which is tapered downward is formed on the top of the dielectric block 511 and a metal film 512 is formed on the bottom of the sample holder hole 511m. That is, in this embodiment, the part of the dielectric block 511 around the sample holder hole 511m forms the sample holder frame.

The turn table 20 (FIG. 1) of the surface plasmon resonance sensor has a plurality of chip holding holes 20w which is of a quadrilateral in shape. Each of the chip holding holes 20w is tapered downward to conform to the outer shape of the dielectric block 511.

The measuring chip 510 is inserted into the chip holding hole 20w from above and is held on the turn table 20 by way of engagement between the outer surface of the dielectric block 511 and inner surface of the chip holding hole 20w. Since the measuring chip 20w is positioned and held by way of engagement between the outer surface of the dielectric block 511 and the inner surface of the chip holding hole 20w which are both of quadrilateral in shape, the dielectric block 511 can be automatically oriented with respect to the turn table in the horizontal direction and cannot be moved from the position in the horizontal direction. With this arrangement, positioning of the measuring chip 510 in the horizontal direction is facilitated.

Further, since the outer surface of the dielectric block 511 and the inner surface of the chip holding hole 20w are both tapered downward, the measuring chip can be automatically located also in the vertical direction. In the measuring chip 510 of this embodiment, the part of the dielectric block 511 lower than the chained line in FIG. 11 projects downward beyond the lower edge of the turn table 20.

Figure 12A:
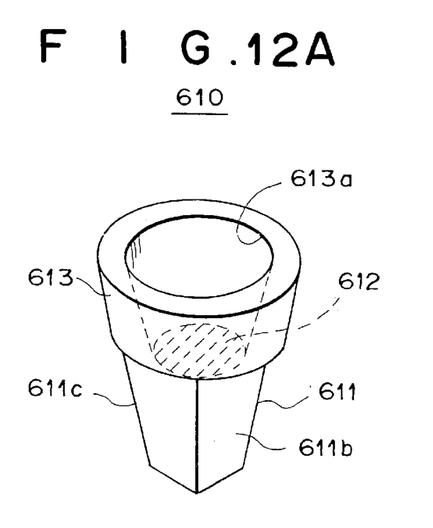
FIG. 12A is a perspective view of a measuring chip in accordance with an eighth embodiment of the present invention.
Figure 12B:
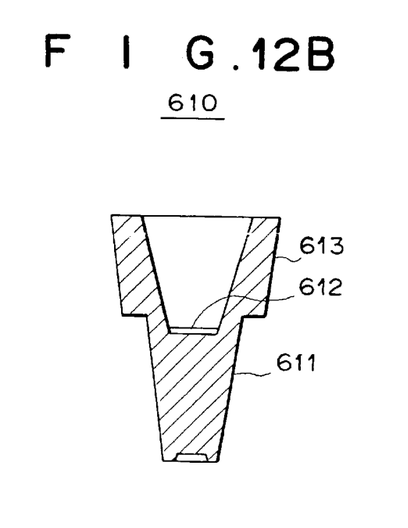
FIG. 12B is a side cross-sectional view of a measuring chip in accordance with the eighth embodiment of the present invention.

The measuring chip 610 of the eighth embodiment shown in FIGS. 12A and 12B differs from that 510 of the seventh embodiment in that a conical sample holding frame 613 provided with a conical sample holding hole 613a tapered downward is formed on the dielectric block 611 integrally therewith. A metal film 612 is formed on the bottom of the sample holding hole 613a.

The dielectric block 611 of the measuring chip 601 of this embodiment is basically the same in the outer shape as the dielectric block 510 of the seventh embodiment. Out of the four side faces of the dielectric block 511, two side faces form a light incident face 511b and a light emanating face 511c. Since the dielectric block 611 is basically the same as that of the seventh embodiment in the outer shape, also the measuring chip 610 of this embodiment can be easily positioned in both the horizontal and vertical directions.

Figure 13:
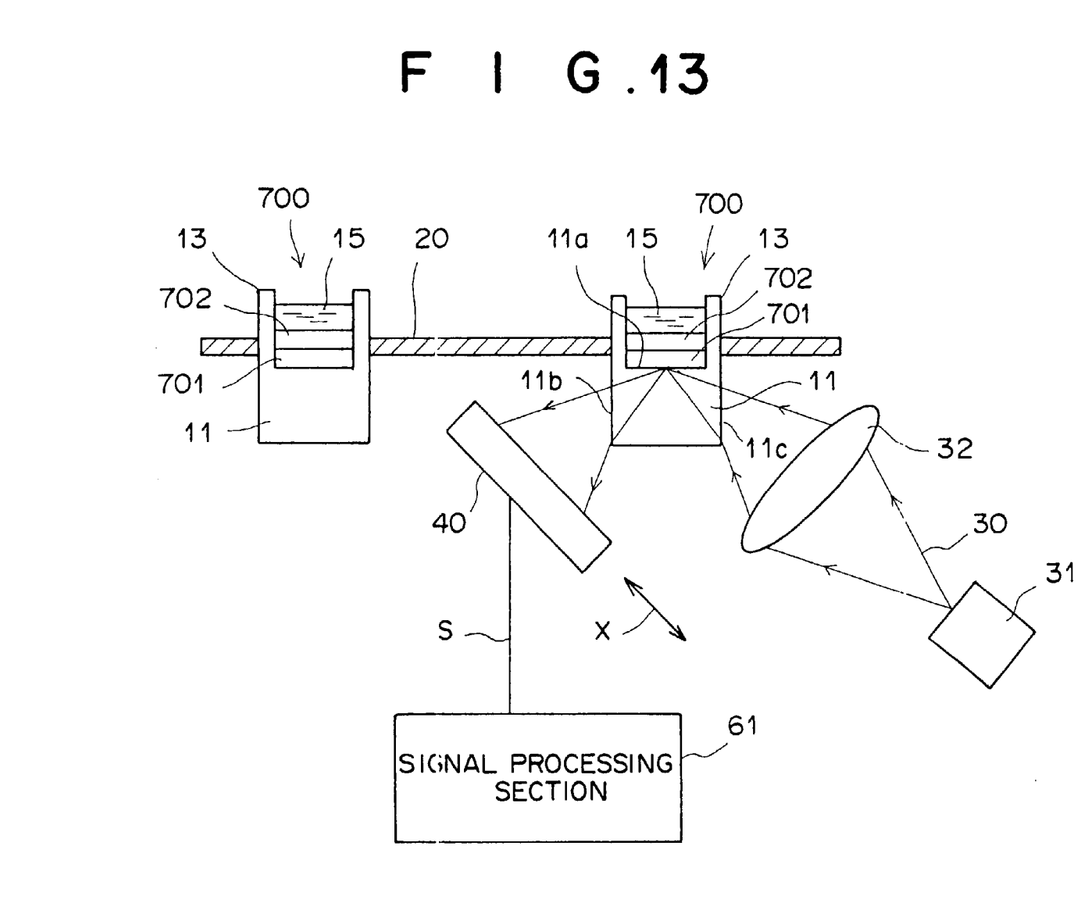
FIG. 13 is a side cross-sectional view partly cut away showing a measuring chip in accordance with a ninth embodiment and a leaky mode sensor employing the measuring chip.

FIG. 13 is a side cross-sectional view partly cut away showing a measuring chip 700 in accordance with a ninth embodiment and a leaky mode sensor employing the measuring chip 700. The leaky mode sensor is basically of the same structure as the surface plasmon resonance sensor shown in FIG. 2. The measuring chip 700 comprises a dielectric block 11, a clad layer 701 formed on the top surface of the dielectric block 11 and an optical waveguide layer 702 formed on the clad layer 701.

The dielectric block 11 is formed of, for instance, synthetic resin or optical glass such as BK7. The clad layer 701 is formed of dielectric material lower than the dielectric block 11 in refractive index or metal such as gold. The optical wave guide layer 702 is formed of dielectric material such as PMMA which is higher than the clad layer 701 in refractive index. The thickness of the clad layer 701 is 36.5 nm when it is formed gold film, and the thickness of the optical waveguide layer 702 is about 700 nm when it is formed of PMMA.

In the leaky mode sensor, when the light beam 30 emitted from the laser 31 is caused to impinge upon the clad layer 701 at an angle not smaller than an angle of total internal reflection, the light beam 30 is reflected in total internal reflection at the interface 11a of the dielectric block 11 and the clad layer 701, and only light having a particular wave number and impinging upon the waveguide layer 702 at a particular angle of incidence comes to propagate through the optical waveguide layer 702 in a waveguide mode after passing through the clad layer 701. When the waveguide mode is thus excited, almost all the incident light is taken in the optical waveguide layer 702 and accordingly, the intensity of light reflected in total internal reflection at the interface 11a of the dielectric block 11 and the clad layer 701 sharply drops. That is, attenuation in total internal reflection occurs.

Since the wave number of light to be propagated through the optical waveguide layer 702 in a waveguide mode depends upon the refractive index of the sample 15 on the optical waveguide layer 702, the refractive index and/or the properties of the sample 15 related to the refractive index can be detected on the basis of the angle of incidence at which the attenuation in total internal reflection occurs. A signal processing section 61 quantitatively analyzes the particular material in the sample 15 on the basis of this fact and the result of the analysis is displayed by the display section (not shown).

As the measuring chip 10 of the first embodiment, the measuring chip 700 of this embodiment need not be coupled with another dielectric block by way of refractive index matching fluid, it is very easy to handle. Further, since it is not necessary to use the refractive index matching fluid, adverse influence of the fluid on the environment can be avoided.

A measuring chip 810 in accordance with the tenth embodiment of the present invention will be described with reference to FIGS. 14, 15A and 15B, hereinbelow.

Figure 11:
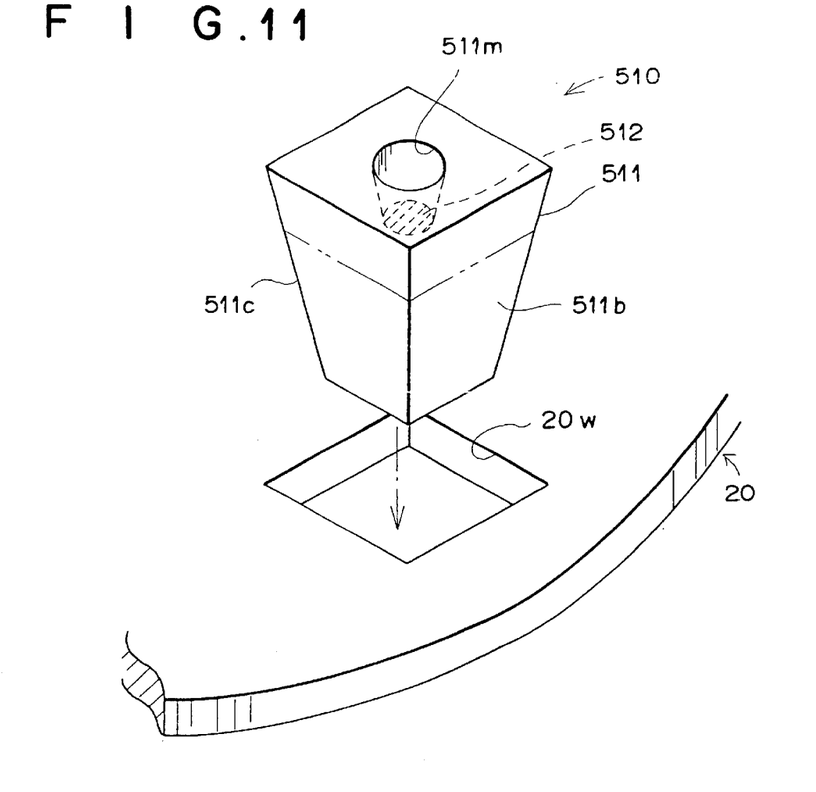
FIG. 11 is a perspective view of a measuring chip in accordance with a seventh embodiment of the present invention.

The measuring chip 810 of this embodiment is substantially the same as the measuring chip 510 of the seventh embodiment shown in FIG. 11 except the shape of the sample holder hole 811m. That is, the measuring chip 810 comprises a dielectric block 811 formed of transparent resin. The dielectric block 811 is of a quadrangular pyramid in outer shape which flares upward and is positioned with the smaller side down when it is set on the surface plasmon resonance sensor.

Out of the four side faces of the dielectric block 811, two side faces form a light incident face 811b and a light emanating face 811c. The light incident face 811b and the light emanating face 811c of the dielectric body 811 may be transparent over the entire area or may be transparent only the part through which the light beam 30 travels. The other two faces may be transparent over the entire area or may be transparent only the part through which the light beam 30 travels, or may be semitransparent.

A sample holder hole 811m which is tapered downward is formed on the top of the dielectric block 811 and a metal film 812 is formed on the bottom of the sample holder hole 811m. That is, in this embodiment, the part of the dielectric block 811 around the sample holder hole 811m forms the sample holder frame.

When the dielectric block 811 is formed of transparent resin, plastic injection molding is generally employed. In plastic injection molding, when the product cannot be smoothly ejected from the injection mold, the product becomes of an irregular shape and a defective product is generated. The dielectric block 511 shown in FIG. 11 can be relatively smoothly ejected from the injection mold since the sample holder hole 511m is tapered. However, a sharp edge defined between the side wall of the sample holder hole 511m and the bottom of the same can adversely affect ejection of the product.

To the contrast, in the measuring chip 810 of the tenth embodiment, the sample holder hole 811m is formed like a bowl and the side wall of the sample holder hole 811m smoothly merges into the bottom of the same, the product can be ejected so smoothly from the injection mold that generation of defective products is suppressed to produce high yield.

As in the measuring chip 110 shown in FIG. 7, since the sample holder hole 811m is flared upward, the metal film 812 can be formed in a uniform thickness without being adversely affected by the part around the sample holder hole 811m.

Figure 16:
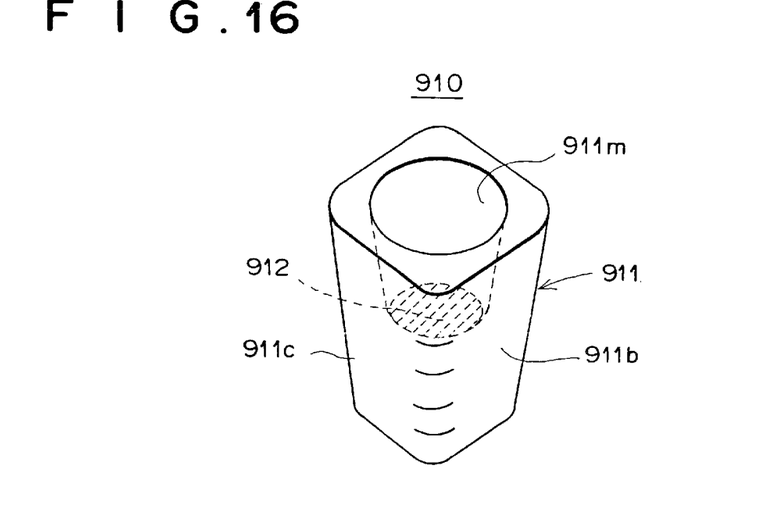
FIG. 16 is a perspective view of a measuring chip in accordance with an eleventh embodiment of the present invention.

A measuring chip 910 in accordance with the eleventh embodiment of the present invention will be described with reference to FIGS. 16, 17A and 17B, hereinbelow.

Figure 14:
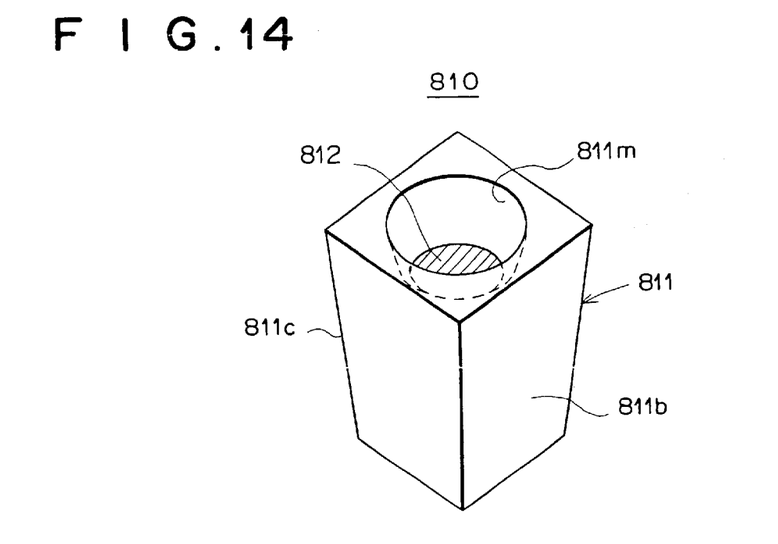
FIG. 14 is a perspective view of a measuring chip in accordance with a tenth embodiment of the present invention.
Figure 15A:
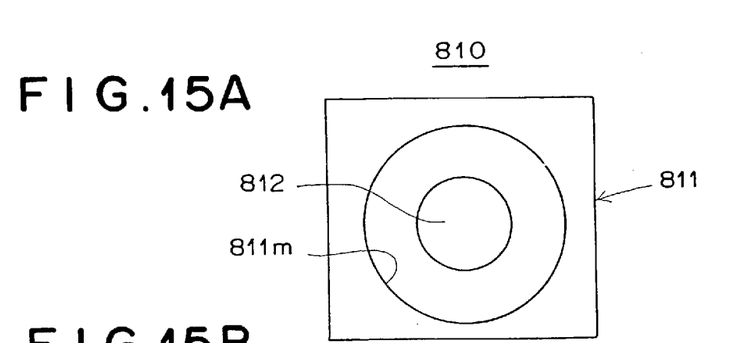
FIG. 15A is a plan view of the measuring chip in accordance with the tenth embodiment of the present invention, FIG. 15B a side cross-sectional view of the measuring chip in accordance with the tenth embodiment of the present invention.
Figure 15B:
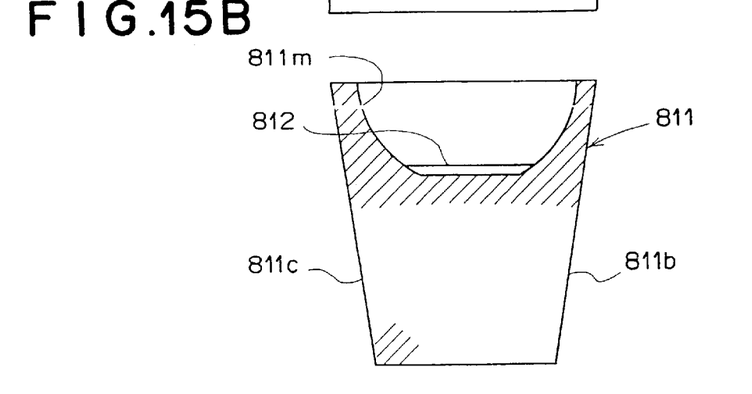

The measuring chip 910 of this embodiment is substantially the same as the measuring chip 810 of the tenth embodiment shown in FIGS. 14, 15A and 15B except the shape of the sample holder hole 911m and the outer shape of the dielectric block 911. That is, the measuring chip 910 comprises a dielectric block 911 formed of transparent resin.

The dielectric block 911 is of a quadrangular pyramid in outer shape which flares upward and is positioned with the smaller side down when it is set on the surface plasmon resonance sensor. Out of the four side faces of the dielectric block 911, two side faces form a light incident face 911b and a light emanating face 911c.

Figure 17A:
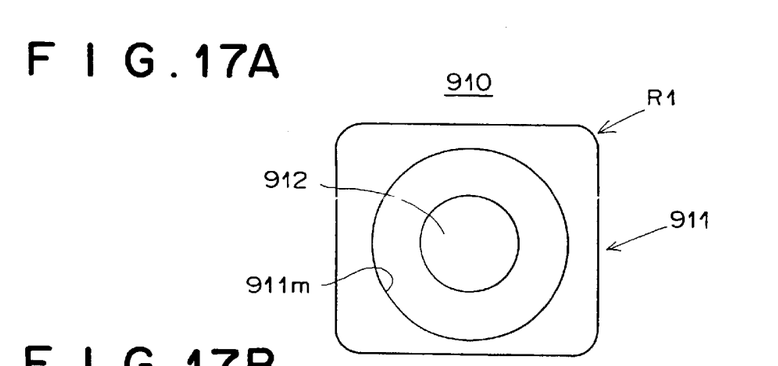
FIG. 17A is a plan view of the measuring chip in accordance with the eleventh embodiment of the present invention, FIG. 17B a side cross-sectional view of the measuring chip in accordance with the eleventh embodiment of the present invention.
Figure 17B:
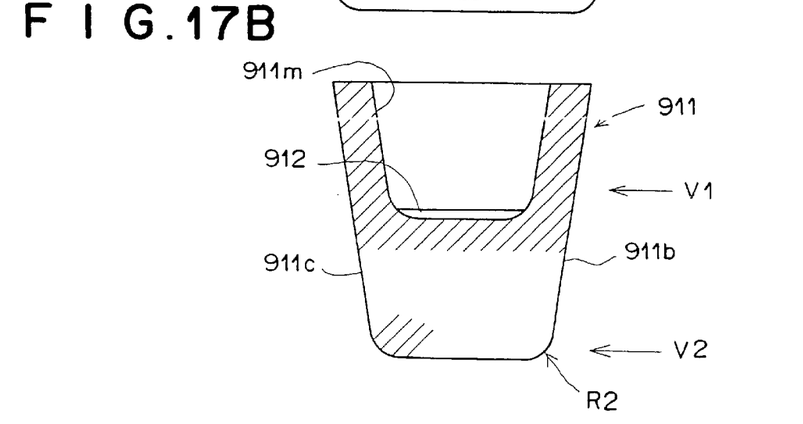

The edges between adjacent side faces of the dielectric block 911 are rounded as indicated by arrow R1 in FIG. 17A, and the corners between the side faces and the bottom face of the dielectric block 911 are rounded as indicated by arrow R2 in FIG. 17B. That is, in both the horizontal cross-sections denoted by arrows v1 and v2, the corners of the dielectric block 911 are rounder.

When the dielectric block 911 is formed by plastic injection molding, the rounded edges and the rounded corners permit the product to be smoothly ejected from the injection mold and suppress generation of defective products, whereby high yield is obtained.

The shapes of the dielectric blocks 811 and 911 of the measuring chips in accordance with the tenth and eleventh embodiments of the present invention may be also applied to the leaky mode sensor shown in FIG. 13 and provide substantially the same results.

The preferred angle of taper when the dielectric block is shaped in a polygonal in horizontal cross-section and is tapered downward as in the seventh, eighth, tenth and eleventh embodiments will be discussed hereinbelow.

Figure 18:
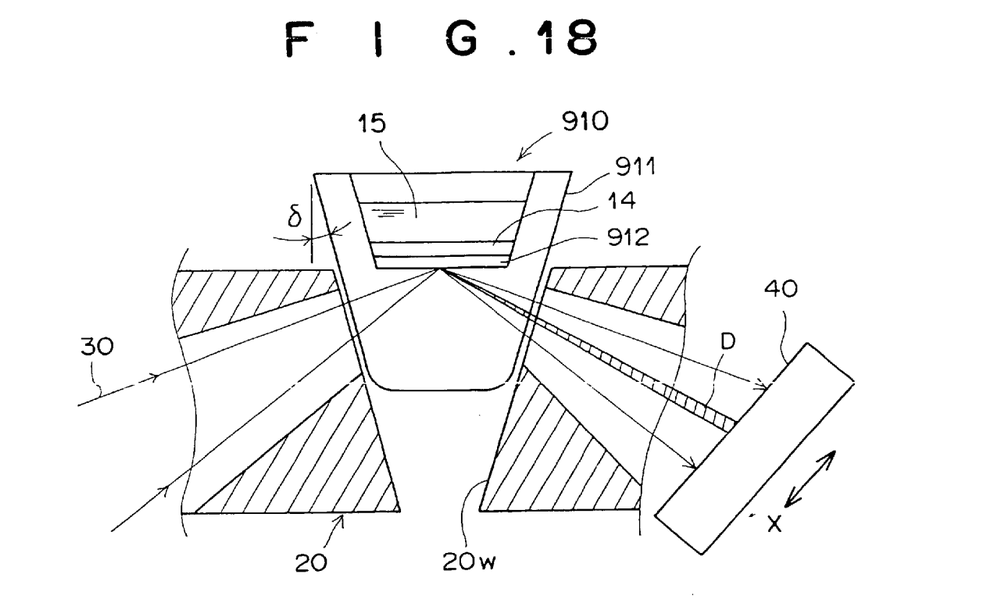
FIG. 18 is a side view partly cut away of an apparatus for investigating a desirable angle of taper of the dielectric block.

We have investigated the range of the preferred angle of taper by the use of the measuring system shown in FIG. 18. The measuring system was basically the same as the surface plasmon resonance sensor shown in FIG. 1. Measuring chips 910 of the eleventh embodiment were set in the chip holding holes 20w of the turn table 20 and the turn table 20 was rotated to bring the measuring chips 910 to the measuring position in sequence. Though not shown, the same light source and photodetector as shown in FIG. 2 were used.

Measuring chips 910 which were 1°, 3°, 7°, 1°, 15° and 20° in angle of taper (δ), the angle between the vertical axis of the dielectric block 911 and the side faces of the same, were prepared, and at the same time, a measuring chip which was 0° in angle of taper δ (not tapered) was prepared. Then the measuring chips were set on respective turn tables which were the same as the angles of taper δ in angle of inclination of the chip holding holes 20w. Sensing medium 14 was fixed on the metal film 912 of each measuring chip and samples containing therein a specific material to be linked with the sensing medium 14.

A component impinging upon the interface of the dielectric block 911 and the metal film 912 at an angle θsp at which attenuation in total internal reflection occurs greatly deteriorates in the intensity of reflected light and the deterioration is observed as a dark line in the reflected light. When the specific material in the sample 15 is linked with the sensing medium 14, the refractive index of the sensing medium 14 is changed and the angle θsp at which attenuation in total internal reflection occurs changes. The change of the angle θsp at which attenuation in total internal reflection occurs is normally within 0.1 to 1.0°. In order to correctly detect the change of the angle θsp at which attenuation in total internal reflection occurs, fluctuation in the measured value of the angle θsp at which attenuation in total internal reflection occurs due to fluctuation in position of the measuring chip 910 should not exceed 1/10 of the range over which the angle θsp changes due to link of the specific material in the sample 15 with the sensing medium 14. That is, fluctuation in the measured value of the angle θsp due to fluctuation in position of the measuring chip should be not larger than 0.01°.

Figure 19:
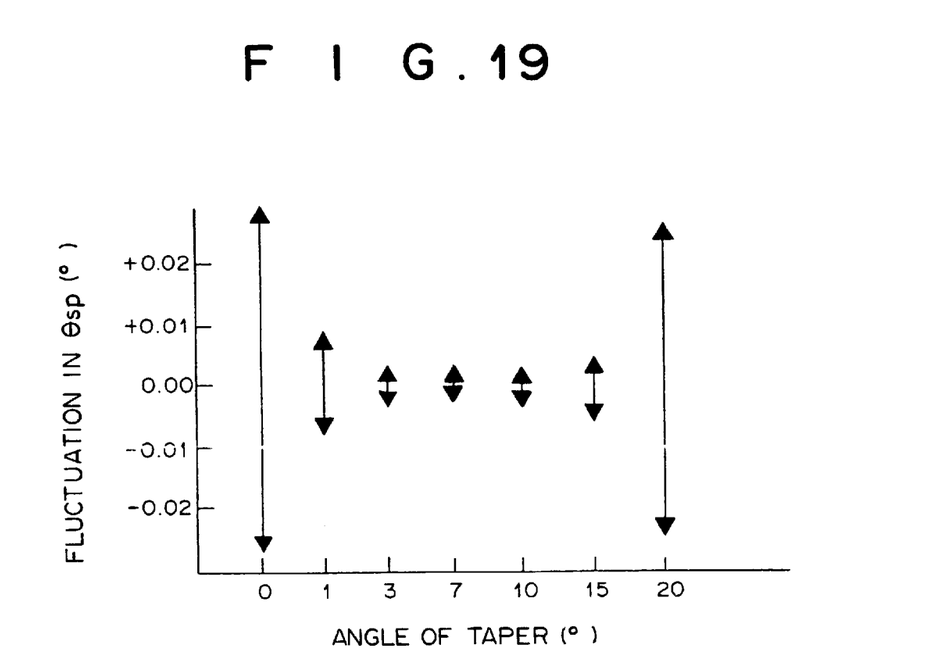
FIG. 19 is a graph showing the result of investigation.

Though the measuring chip is positioned with respect to the chip holder hole 20w of the turn table 20 by virtue of the tapered outer shape of the dielectric block, the measuring chip can be slightly displaced in the vertical direction as the turn table 20 is turned. The displacement of the measuring chip results in fluctuation in measured values of the angle θsp. After link of the specific material and the sensing material was stabilized, the turn tables 20 which were loaded with the measuring chip having different angles of taper δ were turned by one rotation and the difference between the measured values of the angle θsp before and after the rotation. The result is as shown in FIG. 19. As can be understood from FIG. 19, fluctuation in the measured value of the angle θsp due to fluctuation in position of the measuring chip can be not larger than 0.01° when the angle of taper δ is in the range 3 to 15°.

What is claimed is:

1. A measuring chip for a measuring apparatus, comprising:
   a dielectric block;
   a film layer which is formed on a first face of the dielectric block and is brought into contact with a sample;
   a light source which emits a light beam;
   an optical system which causes the light beam to enter the dielectric block through a second face thereof so that the light beam is reflected in total internal reflection at the interface of the dielectric block and the film layer and so that various angles of incidence of the light beam to the interface of the dielectric block and the film layer are obtained;
   photodetector means which detects attenuation in total internal reflection by detecting the intensity of the light beam which is reflected in total internal reflection at the interface and goes outside the dielectric block through a third face thereof; and a sample holder mechanism for holding the sample on the film layer;

wherein the dielectric block of the measuring chip comprises all the first to third faces and the film layer integrally formed on the first face of the dielectric block; and wherein the sample holder mechanism comprises a member which defines above the film layer a space which has closed side walls and is flared upward.

2. A measuring chip as defined in claim 1 in which the inner surface of the member which defines above the film layer the space having closed side walls is smoothly merged with the first face of the dielectric block on which the film layer is formed.

3. A measuring chip as defined in claim 1 in which the dielectric block is substantially polygonal in a horizontal cross-section.

4. A measuring chip as defined in claim 3 in which the corners of the polygonal are rounded in at least one horizontal plane.

5. A measuring chip as defined in claim 3 in which the dielectric block is tapered downward so that the cross-sectional area becomes larger upward.

6. A measuring chip as defined in claim 5 in which the inclined side surfaces of the dielectric block are at 3 to 15° to the vertical axis of the dielectric block.

7. A measuring chip for a leaky mode sensor, comprising:

a dielectric block;

a film layer composed of a clad layer which is formed on a first face of the dielectric block and an optical waveguide layer which is formed on the clad layer and is brought into contact with a sample;

a light source which emits a light beam;

an optical system which causes the light beam to enter the dielectric block through a second face thereof so that the light beam is reflected in total internal reflection at the interface of the dielectric block and the film layer and so that various angles of incidence of the light beam to the interface of the dielectric block and the film layer can be obtained;

photodetector means which detects attenuation in total internal reflection due to excitation of waveguide mode in the optical waveguide layer by detecting the intensity of the light beam which is reflected in total internal reflection and goes outside the dielectric block through a third face thereof; and a sample holder mechanism for holding the sample on the film layer;

wherein the dielectric block of the measuring chip comprises all the first to third faces and the clad layer and the waveguide layer integrally formed on the first face of the dielectric block; and wherein the sample holder mechanism comprises a member which defines above the film layer a space which has closed side walls and is flared upward.

8. A measuring chip as defined in claim 7 in which the inner surface of the member which defines above the film layer the space having closed side walls is smoothly merged with the first face of the dielectric block on which the film layer is formed.

9. A measuring chip as defined in claim 7 in which the dielectric block is substantially polygonal in a horizontal cross-section.

10. A measuring chip as defined in claim 9 in which the corners of the polygonal are rounded in at least one horizontal plane.

11. A measuring chip as defined in claim 9 in which the dielectric block is tapered downward so that the cross-sectional area becomes larger upward.

12. A measuring chip as defined in claim 11 in which the inclined side surfaces of the dielectric block are at 3 to 15° to the vertical axis of the dielectric block.

13. A measuring chip for a surface plasmon resonance sensor, comprising:

a dielectric block;

a metal film layer which is formed on a first face of the dielectric block and is brought into contact with a sample;

a light source which emits a light beam;

an optical system which causes the light beam to enter the dielectric block through a second face thereof so that the light beam is reflected in total internal reflection at the interface of the dielectric block and the metal film layer and so that various angles of incidence of the light beam to the interface of the dielectric block and the metal film layer are obtained;

photodetector means which detects attenuation in total internal reflection due to plasmon resonance by detecting the intensity of the light beam which is reflected in total internal reflection and goes outside the dielectric block through a third face thereof; and a sample holder mechanism for holding the sample on the metal film layer;

wherein the dielectric block of the measuring chip comprises all the first to third faces and the metal film layer integrally formed on the first face of the dielectric block; and wherein the sample holder mechanism comprises a member which defines above the metal film layer a space which has closed side walls and is flared upward.

14. A measuring chip as defined in claim 13 in which the inner surface of the member which defines above the metal film layer the space having closed side walls is smoothly merged with the first face of the dielectric block on which the metal film layer is formed.

15. A measuring chip as defined in claim 13 in which the dielectric block is substantially polygonal in a horizontal cross-section.

16. A measuring chip as defined in claim 15 in which the corners of the polygonal are rounded in at least one horizontal plane.

17. A measuring chip as defined in claim 15 in which the dielectric block is tapered downward so that the cross-sectional area becomes larger upward.

18. A measuring chip as defined in claim 17 in which the inclined side surfaces of the dielectric block are at 3 to 15° to the vertical axis of the dielectric block.

* * * * *